United States Patent [19]

Heald

[11] Patent Number: 4,680,470
[45] Date of Patent: Jul. 14, 1987

[54] METHOD AND APPARATUS FOR CRACK DETECTION AND CHARACTERIZATION

[76] Inventor: Jerry D. Heald, 7145 Via Colina, San Jose, Calif. 95139

[21] Appl. No.: 641,930

[22] Filed: Aug. 17, 1984

Related U.S. Application Data

[63] Continuation-in-part of Ser. No. 565,384, Dec. 27, 1983.

[51] Int. Cl.$^4$ .............................................. G01T 1/169
[52] U.S. Cl. .................... 250/358.1; 378/59; 378/58
[58] Field of Search ............. 250/358.1, 359.1, 363 S, 250/363 R; 378/59, 58

[56] References Cited

U.S. PATENT DOCUMENTS

| | | | |
|---|---|---|---|
| 2,629,831 | 2/1953 | Atchley | 250/358.1 |
| 3,011,057 | 11/1961 | Anger | 250/363 S |
| 3,564,247 | 2/1971 | Packer | 250/358.1 |
| 3,631,247 | 3/1969 | Barton, Jr. | 250/363 R |
| 3,778,613 | 12/1973 | Dorgebray | 250/358.1 |
| 3,849,655 | 11/1974 | Martucci | 250/356.2 |
| 4,172,224 | 10/1979 | Lapinski et al. | 378/58 |
| 4,476,385 | 10/1984 | Wunderlich | 250/303 |

OTHER PUBLICATIONS

Criscuolo, "Slit Det. by Radiography", Material Evaluation, V. 24, N. 4, Apr., 1966.

Primary Examiner—Carolyn E. Fields
Assistant Examiner—Hanig: Richard
Attorney, Agent, or Firm—Thomas E. Schatzel

[57] ABSTRACT

A nondestructive examination method and apparatus for high resolution detection of cracks, defects or anomalies in radioactivity contaminated materials. The method relies upon radioactivity being carried by the normal reactor environment, or by an added radioactive penetrant fluid, to the cracks, defects or anomalies. Detection of this radioactivity by a narrow well defined beam gives an improved measurement of the location and size of the cracks, defects or anomalies. The apparatus includes a sensor mounted on a remotely controlled framework. The sensor includes shielding to direct a very narrow beam of gamma radiation to a scintillation crystal and photomultiplier tube which converts the radiation into electrical signals. The signals are counted by count rate means and converted to digital form and stored. Survey procedures are provided both for detecting cracks and for characterizing cracks once discovered. Computer aided imaging techniques are provided to construct graphical representations from the recorded data.

5 Claims, 9 Drawing Figures

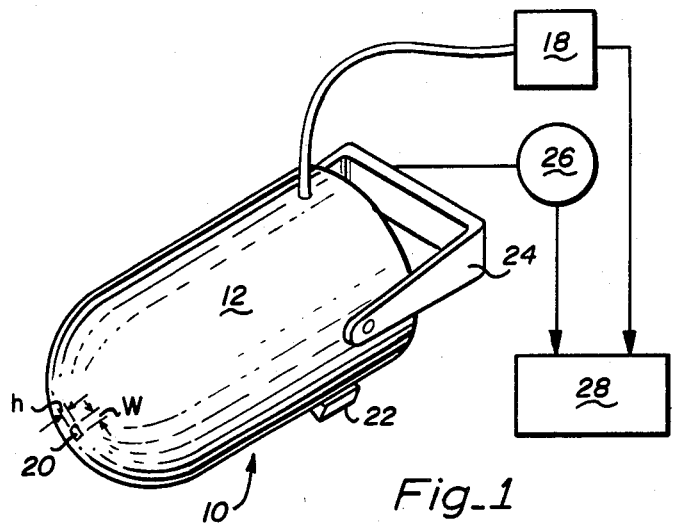
Fig_1
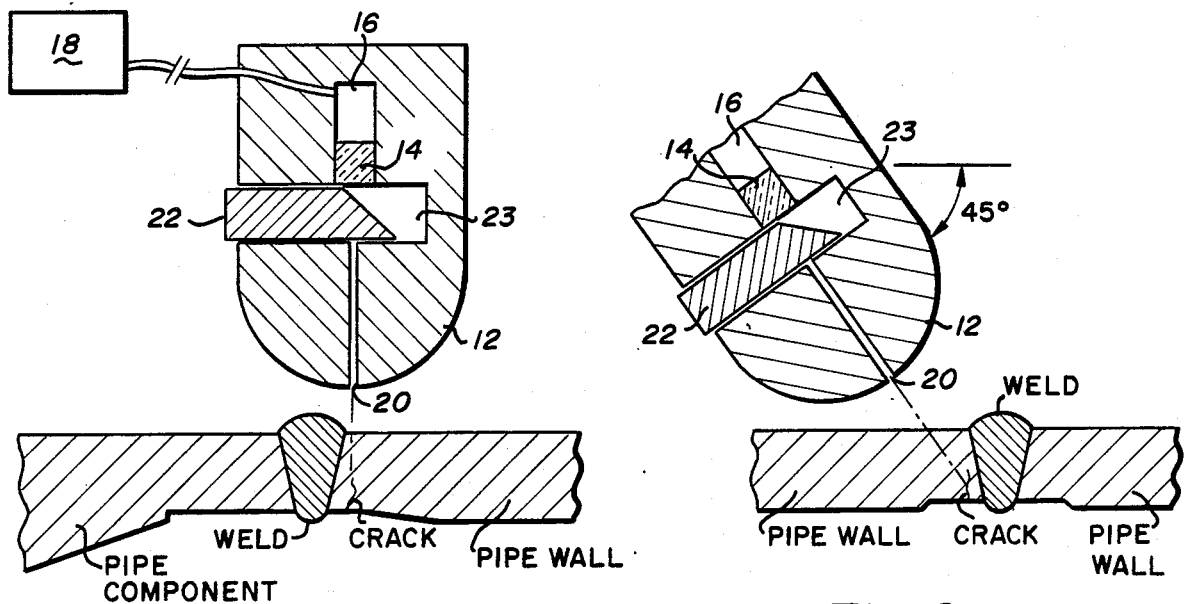
Fig_2
Fig_2a
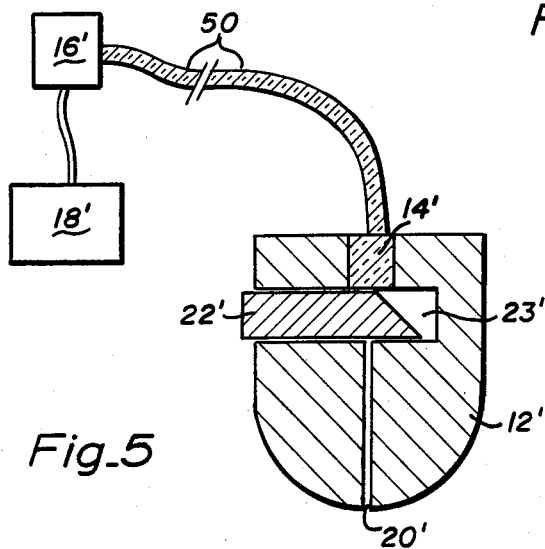
Fig_5

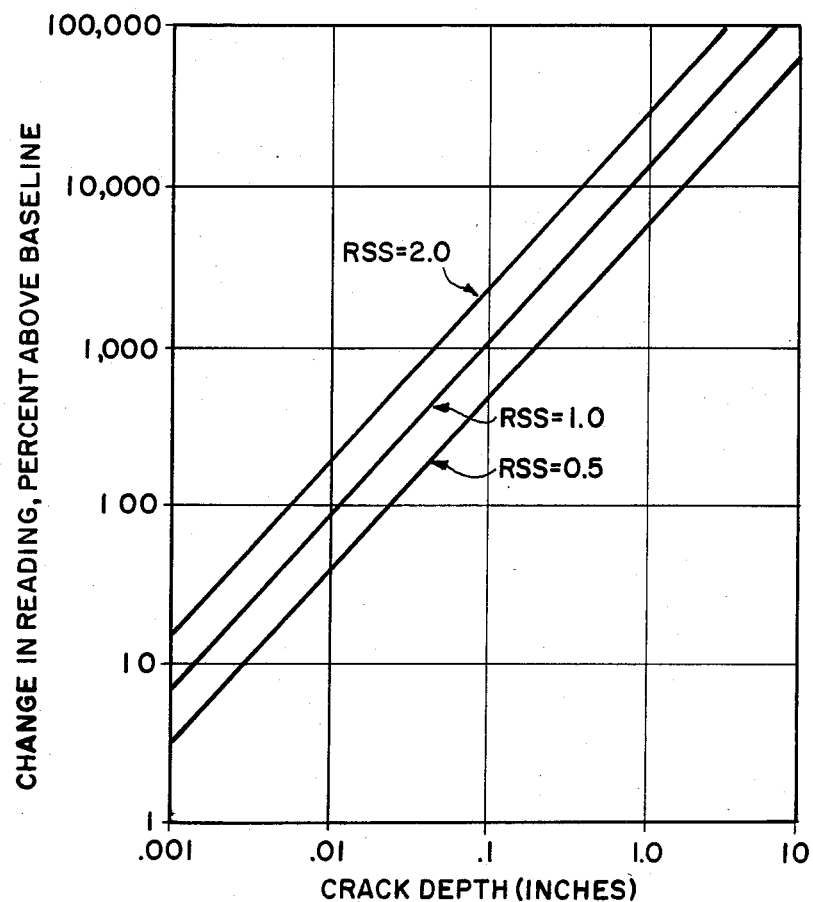
Fig_3
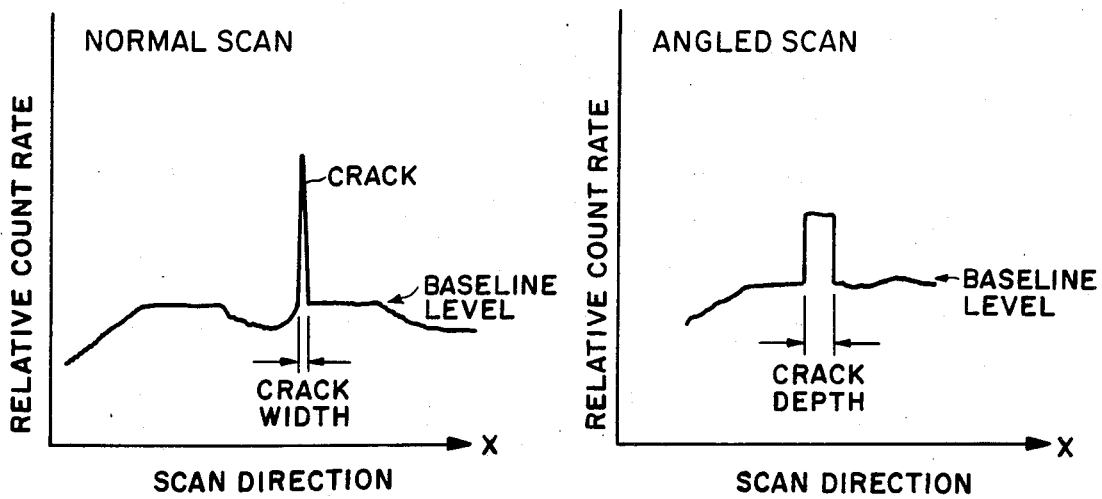
Fig_4      Fig_4a

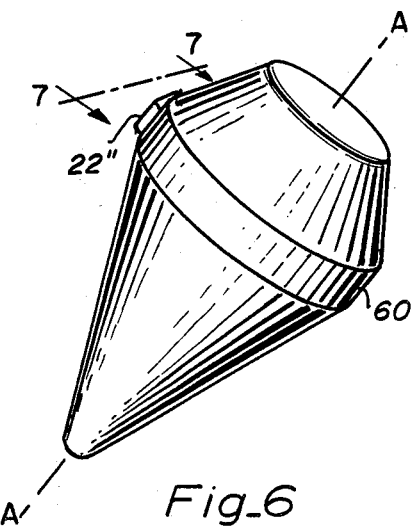
Fig_6
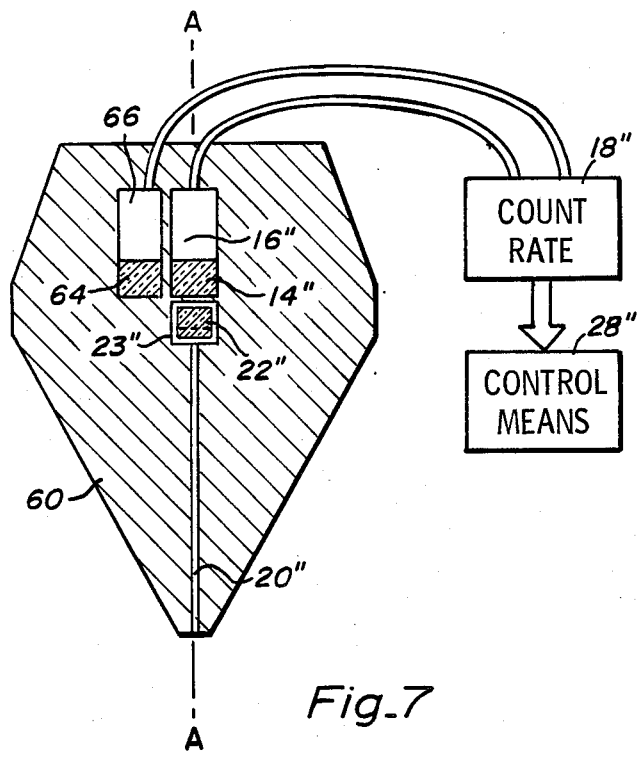
Fig_7

METHOD AND APPARATUS FOR CRACK DETECTION AND CHARACTERIZATION

This is a continuation-in-part of co-pending application Ser. No. 06/565,384 filed on 12/27/83.

BACKGROUND OF THE INVENTION

1. Field of the Invention

This invention relates generally to apparatus and procedures for detecting and characterizing cracks in structures, and more particularly to a sensitive method for detecting and characterizing cracks on the surfaces of piping and equipment of nuclear power plants and on surfaces of other systems and equipment where integrity of the structure is of great importance.

2. Description of the Prior Art

Structural crack detection and characterization is becoming an increasingly important problem in the nuclear power industry. A nuclear power plant contains numerous fluid-carrying components which must be welded together to ensure leak-proof containment of the fluids therein. These components include reactor pumps, valves, piping, piping components and pressure vessels. Flaws or cracks in these components can result from a variety of causes including fabrication errors, cyclic fatigue loads and environmental stress corrosion. Because of the intense heat generated by the welding process combined with environmental factors and stress, cracks sometimes develop in an approximately one-quarter inch zone near the weld, called the heat-affected zone. These cracks can range from no more than a few thousandths of an inch, comprising mere scratches, to much deeper cracks which can grow and lead to eventual structural failure. If cracking is suspected in essential reactor cooling pressure boundaries, substantial non-destructive examination must be performed to allow continued operation or to determine if repairs or replacement of the damaged components are needed. The cost of these inspections and repairs along with replacement power costs is very great. It is believed that a significant portion of these costs could be eliminated if reliable methods were available for early crack detection and characterization.

Various patents have been granted for methods and apparatus for crack detection. Typically, these methods require an external radiation source or input excitation. For example, U.S. Pat. No. 3,934,457 and 3,988,922 issued to Clark, et al. employ conventional ultrasonic examination devices and are limited in their ability to fully detect and characterize cracking. U.S. Pat. Nos. 4,169,758 issued to Blackstone, et al. is similarly limited to an ultrasonic detection apparatus and method.

Present nondestructive examination (NDE) methods of crack detection such as ultrasonic testing, eddy current inspection and acoustic emission, have been only partially successful in locating and establishing the extent of cracking.

SUMMARY OF THE PRESENT INVENTION

Accordingly it is an object of the present invention to provide equipment and procedures for high resolution detection and characterization of structural cracks.

It is a further object of the present invention to provide a method that is passive in that no external radiation sources or input excitations are required.

It is another object of the present invention to minimize nuclear power plant downtime by early detection and accurate characterization of cracking.

It is yet another object of the present invention to provide a scanning method that may be performed remotely to minimize human exposure to radiation and to improve reliability and repeatability.

It is another object of the present invention to provide an apparatus for crack detection which is sufficiently compact and portable so that inspection scans can be made in areas where clearances around the structure are limited.

Briefly, a preferred embodiment of the present invention includes a method and apparatus for detecting and characterizing cracks in radioactively-contaminated structures. The method allows for detection of a defect or anomaly in any structure whose surfaces are contaminated by gamma-emitting isotopes. In addition, the boundaries of the defect can be defined by scanning the structure at a plurality of points with a narrow-beam collimated gamma radiation detector. The data generated can be evaluated using known geometric relationships to produce a graphical representation of the defect or anomaly.

The apparatus includes a detector head collimator assembly which provides shielding from background radiation and contains a narrow aperture for conducting a radiation beam emanating from the internal surfaces being inspected to a gamma radiation detector. The narrow aperture collimates the radiation beam which serves to reduce the amount of extraneous radiation from surrounding materials to an acceptable level. This beam collimation is the means by which the high sensitivity is achieved. Within the detector assembly is a radiation detector comprising a scintillation crystal and a photomultiplier tube. Other types of radiation detectors, such as a Geiger-Muller tube, may be employed, but the scintillation counter has the ability to differentiate between different gamma radiation energies thus allowing isotope identification and selective gamma energy scanning. Such selective energy scanning could significantly increase sensitivity if specific isotopes in the contaminating material deposits are found to concentrate more in cracks than on equipment surfaces. Signals from the radiation detector are fed into count rate instrumentation. This may be a simple count rate system such as a count rate meter or it may be a computerized data acquisition system, depending on the desired crack size detectability limits. In the preferred embodiment signals representing both count rate and orientation of the detector head relative to the inspected surface would be digitalized and recorded on magnetic tape for documentation and post inspection analysis and evaluation.

The detector head collimator assembly itself is mounted on a remotely controlled scanning mechanism. This mechanism is adapted to maintain a constant distance between the inspected surface and the scanning head and to maintain the scanning head at a separation distance which is a minimum possible value. This will maximize sensitivity and minimize corrections for measurement distance. Sensors on the scanning head mechanism are adapted to provide translational and rotational signals for computer analysis. Such positional signals, together with the sensor signal amplitude may be processed by computer assisted imaging means to yield graphical and pictorial representations.

The invention further includes methods for characterizing and mapping structural cracks. For detection, simple axial or circumferential scans can be used to locate crack indications. Once the region of concern has been identified, a more extensive scanning technique can be used to fully characterize the crack including its orientation, length, width, and depth. Scanning will be done initially with the detector head assembly at an angle nearly normal to the inspected surface. At the normal angle, the crack depth is an exponential function of the measured signal amplitude. Crack width is directly proportional to the signal width in the scan direction. Crack length is determined by successive scans in the axial direction. If irregular crack shapes are encountered, the sensor can be tilted in any direction to change the beam angle with respect to the cracked surface to determine crack orientation. These manipulations, resulting in relative signal amplitude changes, should allow for complete characterization of any shape crack.

This inspection method is applicable to essentially all nuclear power plant equipment that has radioactive gamma emitting contamination on suspected cracked surfaces. It may be noted that the source or method of defect contamination is irrelevant to the examination and detection method. Inspectable equipment would include boiling water reactor (BWR) and pressure water reactor (PWR) primary system pressure boundaries such as: pumps, valves, heat exchangers, steam turbines, piping and pressure vessels. PWR secondary systems are also inspectable if sufficient contamination is present. The method and apparatus are particularly important for use in conjunction with the BWR systems. This is because more oxygen is entrained in the BWR fluids. This oxygen contributes to pipe corrosion which results in an increase in the incidence of crackinq. Specially designed detector heads may be produced for smaller internal parts such as heat exchangers, steam generator tubes and turbine internals.

With the selective energy scanning technique employing the scintillation counter in conjunction with a photomultipler tube, it may be possible to scan areas near the nuclear reactor core where neutron flux irradiation causes artificially induced high level gamma radiation. This may be done by focusing the detector on a preselected gamma radiation energy, thereby excluding the high level background radiation so that measurable count rates from internal contamination may be selected and counted. Additionally, this method may be applied to any crack detection in solid structures, as long as crack contamination is present. Thus, even non-nuclear equipment and structures, for example critical aircraft and spacecraft structural components, may be characterized if it were allowable to temporarily contaminate local suspected areas with low level, short half-life gamma emitting isotopes. One such possible structure which may be examined is the human body. Utilizing the selective energy scanning technique and apparatus, particular radioactive isotopes may be identified. It is known that certain isotopes tend to accumulate in specific organs within the body. This may be advantageously employed in "whole body counting" wherein it is desired to ascertain the amount of radioactivity in each organ. By tuning the detector to the particular isotope known to accumulate within the particular organ, the amount of radioactive contamination may be accurately measured. Further, the procedure may be used to obtain a pictorial representation of an organ by doing a series of scans around the organ and at various angles, and processing the resultant data with computer aided imaging techniques. Pinpointing conditions such as clogged arteries may be done using a triangulation technique utilizing a variety of scan angles.

It is an advantage of the present invention that the method is passive requiring no input exitations or external radiation sources.

It is another advantage of the present invention that the method is independent of equipment size, thickness and materials including as-cast materials such as weld deposits.

It is a further advantage of the present invention that sensitivity is superior to existing NDE methods.

It is a further advantage of the present invention that the cracks can be characterized, and their orientations can be determined.

It is a further advantage of the present invention that a graphical representation of the crack can be developed by the imaging technique.

It is yet another advantage of the present invention that measurements are made without the need of direct surface contact.

It is yet another advantage that the scanning procedures may be performed remotely, thus mitigating human radiation exposure.

It is yet another advantage that the apparatus is small in size, thus enabling crack detection in relatively small, confined spaces.

It is a further advantage that the method allows for detection and characterization of any radioactive surface, including those that may be made temporarily radioactive for examination and detection purposes.

These and other objects and advantages of the present invention will no doubt become obvious to those of ordinary skill in the art after having read the following detailed description of the preferred embodiment as illustrated in the various drawing figures.

IN THE DRAWINGS

FIG. 1 is a perspective view of a narrow beam gamma detection apparatus incorporating the present invention;

FIG. 2 is a side sectional view of the detector head assembly of FIG. 1;

FIG. 2a is a side sectional view showing the detector head assembly tilted at a forty-five degree angle;

FIG. 3 is a graph illustrating a theoretical percentage change of count rate as a function of crack depth and relative source strength (RSS);

FIG. 4 is a graph illustrating count rate versus detector position for a normal scan;

FIG. 4a is a graph illustrating count rate versus detector position for a forty-five degree angled scan;

FIG. 5 is a side sectional view of an alternative embodiment of the present invention;

FIG. 6 is a perspective view of a second alternative embodiment of the detector head collimator assembly; and FIG. 7 is a side-sectional view of the detector head collimator assembly of FIG. 6.

DETAILED DESCRIPTION OF THE PREFERRED EMBODIMENT

FIG. 1 illustrates a narrow beam gamma radiation detection apparatus for crack detection and characterization and designated by the general reference character 10. The detector apparatus 10 includes a detector head collimator assembly 12. As shown in FIGS. 2 and 2a the assembly 12 includes a gamma radiation detector comprising a scintillation crystal 14 and a photomultiplier tube 16. Other detector tubes may be employed, for example, a Geiger-Muller tube or a solid state germanium crystal which converts gamma radiation directly into electrical impulses. The scintillation crystal and the germanium crystal systems have the advantage of a higher count rate and the ability to distinguish between different gamma radiation energies. If isotope identification is the primary concern, as for example, in the case of corrosion-induced crackinq where the source of corrosion is of interest, then the germanium crystal may be preferred because of its superior ability to distinguish between different gamma radiation energies. The scintillation crystal 14 is a fluorescent crystal which produces light in response to photoelectric capture of the gamma rays. The produced light is detected and amplified by the photomultiplier tube 16 which is coupled to the scintillation crystal 14. This amplification results in a sufficiently strong electrical signal to activate a count rate device 18. The scintillation crystal 14 and photomultiplier tube can distinguish between different gamma radiation energies because the light pulse and resulting electrical impulse are proportional to the energy of the radiation captured by the crystal. This will allow isotope identification and selective gamma energy scanning. The count rate device 18 is, in the preferred embodiment, a simple count rate system. Such a count rate system includes high and low voltage power supplies, a preamplifier, a main amplifier, a discriminator, a single channel analyzer and a count rate module with an electrical output directly proportional to the measured count rate. This system, in conjunction with an X-Y recorder for recording the positional changes of the detector head collimator assembly 12, will allow for detection and chacterization of cracks. For more detailed crack detection and characterization, including imaging of the crack, the count rate system may be embodied in a computerized data acquisition system. Such a system is capable of recording the signals from the count rate system and from various positional transducers as data sets which can be manipulated to provide a pictorial or graphical representation for evaluation. To attain the desired sensitivity for detection and characterization of the cracks, the count rate system 18 should be designed to cover a range of at least four orders of magnitude. As shown by FIG. 3, this will allow for resolution of cracks which range in depth from one-thousandth of an inch to one inch. The detector head collimator assembly 12 is constructed of a heavy metal such as lead, uranium or tungsten to shield the scintillation crystal from unwanted gamma radiation. Uniform shielding is accomplished by constructing the detector head collimator assembly 12 in a spherical or hemispherical shape, with from one to four inches of shielding around the scintillation crystal. In the preferred embodiment, the detector head assembly is formed of lead or tungsten and is hemispherical in shape. A beam slit 20 is located in the detector head assembly 12 and allows passage of gamma radiation energies to the scintillation crystal 14. The beam slit 20 further serves to collimate the gamma radiation energies eminating from the surface being examined, thus confining the radiation measurements to a very small volume of contaminated material. This is necessary to attain the high resolution needed for characterization. The highest sensitivity for linear cracks will be obtained by employing a rectangular slit with a height (h) of one hundredth of an inch and a width (w) of two hundredths of an inch as shown in FIG. 1. A circular slit, however, will also give extremely high sensitivities and may be employed as well. Calculations show that a slit diameter or height of from one to two hundredths of an inch will yield the maximum sensitivity. Additionally, the beam spread angle should be controlled to the minimum practical value - on the order of ten degrees or less. This angle is defined as the arctangent of the slit height (h) or diameter (d) divided by the length (1) of the shielding slit 20. By maintaining a small angle, the distance between the detector and the surface being inspected becomes less significant.

Intermediate to the slit 20 and the scintillation crystal 14 is a variable thickness shielding shim 22. Shim 22 is used to establish a baseline radiation level against which the other readings may be compared. The shim 22 is a wedge-shaped piece of shielding material which may be slid into a slot 23 in the detector head collimator assembly 12. This slot 23 is intermediate to the scintillation crystal 14 and the beam slit 20 and is perpendicular to the beam slit 20. The wedge shape of the shim 22 allows for variation in the amount of shielding material that is placed in the radiation path. In this way, a measurable count rate can be obtained even with heavy gamma radiation sources, simply by urging more of the wedge across the beam slit. The baseline count rate is thus selected arbitrarily based on radiation levels. Alternatively, the baseline may be selected by reducing the count rate electrically within the count rate system 18. This achieves the same result as the shim 22 and may allow for the elimination of the shim 22 and the slot 23.

As shown schematically in FIG. 1, the detector head collimator assembly 12 is mounted on a remotely controlled scanning mechanism 24, which is adapted to move the head 12 in both axial and circumferential scan directions. The mechanism 24 is designed to hold the detector head 12 in proximity with the inspected surface and to maintain the separation distance uniformly and at the minimum possible value. This value is typically about one-quarter to one-half an inch, which is sufficient to clear the welds. The mechanism itself may be of a type known in the art which can automatically or semiautomatically follow the exterior or interior surfaces of a vessel being inspected. Examples of such mechanisms are disclosed in U.S. Pat. No. 3,988,922, issued to Clark et al., and in U.S. Pat. No. 4,169,758, issued to Blackstone et al.. The mechanism 24 may include a stepper motor 26 for each axis of motion of the mechanism 24. Only one motor 26 is shown in schematic in FIG. 1. The stepper motors 26 are electronically coupled to a programmable automatic control means 28 which both directs the operation of each motor and records the amount of movement of the mechanism 24 in each direction relative to a preselected, arbitrary starting point. In this way the detector head collimator assembly 12 may be precisely located about the structure being examined, and the location may be recorded by the control means 28 and paired with a measured gamma radiation value at each location so that a graphical representation may be developed. Because of space limitations associated with most nuclear power plant equipment, the overall size of the detector head assembly 12 and of the scanning mechanism 24 must be minimized. The remotely controlled mechanism 24 serves to minimize operator exposure to hazardous radiation, and may be partially or fully automated.

The method employed is designed to take advantage of the radioactive contamination film or layer that normally exists on the internal surfaces of nuclear power plant equipment. Where internal cracks are present, the surfaces of the cracks will also be covered with a contamination film. A ratio between the amount of radioactive contamination on the internal surfaces of the equipment and the amount of radioactive contamination on the cracked surface can be determined by experimental calibration procedures and accounted for in theoretical predictions. Crack detection, depth predictions and crack characterizations in the normal angle scanning mode are based on measurements of relative signal amplitudes resulting from the ratio between the internal surface contamination versus the cracked surface contamination. Any one measurement will be the sum of the general background radiation plus the reading from the inside surface contamination plus an amount due to the crack contamination, if a crack exists at the measurement location. A baseline reading is taken at a point in the vicinity of, but away from a crack indication. This baseline reading becomes the reference value about which all other readings in the same general area will be compared. The total baseline reading is designated $R_{TB}$ and is given by:

$$R_{TB} = R_{GB} + R_{SC}, \tag{1}$$

where
$R_{GB}$ = General Background Reading, and
$R_{SC}$ = Reading due to inside surface contamination At a crack location, a larger reading will be observed. This reading, designated total reading $R_T$, is given by:

$$R_T = R_{GB} + R_{SC} + R_C, \tag{2}$$

where $R_C$ = Reading due to crack contamination. To normalize the output signal to the total baseline, the ratio of the readings is taken as follows:

$$R_T/R_{TB} = \frac{R_{GB} + R_{SC} + R_C}{R_{GB} + R_{SC}}; \tag{3}$$

and $$R_T/R_{TB} = 1 + \frac{R_C}{R_{GB} + R_{SC}}.$$

To simplify the calculational procedure, a reading of the general background only is taken and recorded ($R_{GB}$) Then a reading including surface contamination is taken and recorded ($R_{TB}$). By subtracting, the amount due to surface contamination ($R_{SC}$) can be determined i.e.;

$$R_{SC} = R_{TB} - R_{GB}.$$

The ratio of $R_{GB}/R_{SC}$ is then formed and the result is set equal to a parameter alpha ($\alpha$) i.e.;

$$R_{GB}/R_{SC} = \alpha \tag{4}$$

Substituting equation (4) into equation (3) yields:

$$R_T/R_{TB} = 1 + \frac{R_C}{(1 + \alpha)R_{SC}} \tag{5}$$

This is a normalized expression for the relative reading as a function of $R_C$, $R_{SC}$ and the parameter $\alpha$. $R_C$ and $R_{SC}$ can each be calculated from a theoretical basis independent of the background radiation and $\alpha$ can be determined experimentally at the time and location the measurements are made.

The effect of $\alpha$ in equation (5) is to decrease the sensitivity of the system output as $\alpha$ increases. Therefore, it is important to provide sufficient shielding to minimize the general background radiation reading.

Equations describing the expected theoretical readings, $R_C$ and $R_{SC}$ have been derived and are given as follows:

$$R_C = 2/\mu f_c w \, S_c''' e^{-\mu t}(e^{\mu a} - 1), \text{ and} \tag{6}$$

$$R_{SC} = 2wh \, f_{SC} S_{SC}''' e^{-\mu t}. \tag{7}$$

The results given in equations (6) and (7) are for a narrow rectangular collimated beam of width (w) and height (h). Slightly different results are obtained for other beam shapes, such as a circular beam. Theoretically, the rectangular beam will give the highest sensitivity for linear cracks. However, a circular beam will also give extremely high sensitivities and is probably more practical. The other parameters in equations (6) and (7) are defined and described below. Combining equations (5), (6), and (7) results in:

$$R_T/R_{TB} = 1 + \frac{1}{\mu h(1 + \alpha)} \frac{f_c S_c}{f_{SC} S_{SC}} (e^{\mu a} - 1), \tag{8}$$

which is the theoretical prediction for the relative reading using a rectangular beam. Note that the beam width (w) and material thickness (t) have cancelled out in equation (8) and therefore do not effect the relative output used to predict crack depths. The only restriction on its use is that the minimum beam height (h) be greater than or equal to the expected linear crack width. This restriction is purely analytical to ensure that the assumed geometries and area assumptions will be maintained.

The other parameters in equation (8) are:
$\mu$ = Linear attenuation coefficient;
$\alpha$ = Background ratio, see equation (4);
$f_c$ = Contamination film thickness (crack surfaces);
$f_{SC}$ = Contamination film thickness (equipment surfaces);
$S_c'''$ = Volumetric source strength (crack surfaces);
$S_{SC}'''$ = Volumetric source strength (equipment surfaces; and
a = Crack depth from inside surface.

If a circular beam were used, the factor $1\mu h$ in equation (8) would change to $4/\mu\pi d$; where (d) would be the beam diameter. In this case the minimum beam diameter would be approximately ten times the expected crack width. Since either form of equation (8) results in beam dimensions in the denominator of the second term, the sensitivity is inversely proportional to beam size. Finally, since (h) can be made smaller than (d), at the minimum size limits, a rectangular beam can be more sensitive than a circular beam.

The quantity ($f_c S_c/f_{SC} S_{SC}$) in equation (8) is the total relative source strength (RSS) between the crack surfaces and the equipment surfaces. Since each value ($f_c$, $f_{SC}$, $S_c$, $S_{SC}$) will be difficult to establish individually, the entire quantity will be combined into one parameter for evaluation. In addition, this quantity (RSS) is the primary factor to be determined during calibration work.

A numerical evaluation of this method's performance using the normal-angle scan only, and based on equation (8) may be done using the following assumed values for the parameters:

Rectangular Beam (h)=0.01 inches
Attenuation Coefficient ($\mu$)=1.07 inches $^{-1}$ for steel,
Background Ratio ($\alpha$)=0.18,
Relative Source Strength (RSS) =0.5, 1.0, 2.0, and
Crack Depth (a) =0.001 to 1.0 inches.

The results are plotted on FIG. 3 which gives the percent changes in relative reading as a function of crack depth (a) and Relative Source Strength (RSS). The results show extremely high sensitivity to crack depth. Based upon detection of a five percent change in count rate, these results show that a 0.001 inch crack can easily be detected even with a thick wall structure. Cracks of engineering significance, 0.05 inches or greater, will give signal changes of more than one hundred percent.

To detect cracks or anomalous areas of radiation concentration, simple axial or circumferential scans may be employed. These scans are performed with the detector head collimator assembly 12 positioned at a normal angle relative to the scanned surface, as shown in FIG. 2. A graph of count rate versus detector position for this type of scan is illustrated in FIG. 4, and it can be seen that the amplitude of the count rate signal is a function of the depth of the crack. For efficiency, the scanning mechanism 24 will be capable of operating at two or more scanning speeds. Initially a fast scan will be employed to rapidly locate areas of concern. Once an indication has been identified, a more extensive scanning technique, at a slower speed, can be used to fully characterize the cracking. If irregular crack shapes, for example, curved or branched cracks are encountered, the sensor can be tilted in any direction to change the beam angle with respect to the cracked surface. With the angled scan, the crack depth is a function of the scan angle and distance, and is not a function of signal amplitude. In this mode, amplitude changes are used only to define the boundaries of the contaminated regions. This method may be used to supplement data from a normal-angle scan, or it may be used independently to determine crack sizes. As shown in FIG. 2a, a tilt angle of forty-five degrees gives a one to one ratio of crack height to scanning distance. The resulting graph of count rate versus detection position for the forty-five degree tilt angle is illustrated in FIG. 4a.

An alternative embodiment of the detector head collimator assembly is illustrated in FIG. 5 and designated by the general reference character 12'. Those elements of the alternative embodiment which are common to the preferred embodiment carry the same reference numeral distinguished by a prime designation. This assembly is similar to the detector assembly 12 with the omission of the photomultiplier tube 16 and with the addition of a flexible lightguide cable 50. The elimination of the tube 16 is designed to further reduce the size of the head assembly 12' for greater operating flexibility. The lightguide cable 50 is optically coupled to the scintillation crystal 14' and transmits the produced light to a remote photomultiplier tube 16' which is mounted outside of the assembly 12' and can be several feet away depending upon the type of lightguide employed. The remaining elements of the assembly 12' and the rest of the apparatus are identical with those of the preferred embodiment.

A second alternative embodiment of the detector head collimator assembly is illustrated in perspective in FIG. 6 and in section in FIG. 7 and referred to by the general reference character 60. Those elements of the alternative embodiment common to the preferred embodiment carry the same reference numeral distinguished by a double prime designation. The assembly 60 incorporates an additional gamma radiation detector, comprising a scintillation crystal 64 and a photomultiplier tube 66, in addition to a scintillation crystal 14" and photomultiplier tube 16". Other detector devices, for example, a Geiger Mueller tube or a solid state germanium crystal may also be employed, however, the crystal 64 and photomultiplier tube 66 can measure higher count rates and have the ability to distinguish between different gamma radiation energies. The collimator head 60 is constructed of a heavy metal such as lead, uranium or tungsten to shield the scintillation crystals 14" and 64 from unwanted gamma radiation. A beam slit 20" is located in the detector head collimator assembly 60 about a central axis A of rotation thereof, and allows for the passage of gamma radiation energies to the scintillation crystal 14" only. As in the detector head collimator assembly 12, a variable thickness shielding shim 22" may be positioned within a slot 23" intermediate to the beam slit 20" and the scintillation crystal 14". To avoid varying the gamma radiation energies reaching the crystal 64, the crystal 64 and tube 66 are positioned to the side of the shim 22" and slot 23", as illustrated in FIG. 7 which shows the shim 22" and slot 23" in an end view. It may be noted that the shim 22" and slot 23" may be omitted and the count rates reduced electronically in a count rate device 18".

The additional scintillation crystal 64 is positioned adjacent to the crystal 14" and is not provided with any means for allowing radiation to reach it, other than through the walls of the detector head collimator assembly 60. The second scintillation crystal 64 thus advantageously acts as a baseline or zero detector for the apparatus. The second crystal 64, being positioned very close to the first crystal 14", will receive all the gamma radiation energies received by the crystal 14" with the exception to those energies directed through the beam slit 20". As in the apparatus 10, the scintillation crystals 14" and 64 are coupled to the photomultiplier tubes, 16" and 66, respectively which provide an electrical output to the count rate device 18". By subtracting the count rate produced by the crystal 64 from the count rate produced by the crystal 14" a result is obtained which is the count rate from the contaminated source only. The detector head collimator assembly 60 thus allows single pass scanning of the contaminated area, without the need for a separate pass to obtain a baseline reading. Additionally, the proximity of the crystals 14" and 64 improves the accuracy of readings taken by the detector head collimator assembly 60 by providing a simultaneous baseline. It may be noted that the count rate manipulations may be done automatically by the count rate device 18", or by the use of separate count rate devices 18" for each scintillation crystal 14" and 64, with subsequent calculations performed by a control means 28".

Besides reducing the number of passes required, the addition of the second scintillation crystal 64 renders the shape of the detector collimator head 60 less critical. Because the second crystal 64 receives essentially all background radiation received by the crystal 14", uniformity of the shielding is less important. To provide substantially uniform shielding thickness in all directions, the detector head collimator 60 is fabricated, for example, in a frustro-conical shape, with the beam slit 20" extending from the narrow portion of the cone. By using the second scintillation crystal 64 to provide a continuous baseline reading, virtually any head shape may be used, including oblong or rectangular shapes.

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall wthin the true spirit and scope of the invention.

I claim:

1. A nondestructive examining method for detecting and characterizing anomalies in radioactively-contaminated structures comprising:
    placing a gamma radiation detector in proximity to a surface of a structure to be examined, said detector including a radiation-proof housing with a beam slit therein for conducting gamma radiation from only a very small volume of material to said detector, said detector further including conversion means coupled thereto to convert said radiation to electrical signals;
    scanning said surface while maintaining said detector in proximity to said surface;
    measuring and recording said gamma radiation emitted by said structure at a plurality of points about said structure and at various angles relative to the surface, the measuring of gamma radiation including measuring at each point and angle the general background radiation and the radiation due to the inside surface contamination and crack contamination and further measuring and recording a location of said housing relative to a predetermined starting point on said structure for each of said plurality of points wherein gamma radiation is measured, and pairing said measurement locations with said gamma radiation measurements, such that a plurality of data sets, comprising positional coordinates paired with radiation level values are generated; and
    comparing the amount of radiation detected at each point and angle with the amount detected at each preceding point and angle along each scan direction, such that a graphical representation, including depth, of the anomaly may be developed at each scan location.

2. The method of claim 1 wherein
    a baseline reading of gamma radiation is obtained by measuring and recording said radiation emitted about a plurality of points located away from suspected anomalies, said baseline comprising a relatively constant radiation level over said points and being used as a reference value to which all other readings are compared.

3. The method of claim 2 wherein
    said data points are processed utilizing computer aided processing means such that a pictorial representation of the anomaly is, developed.

4. The method of claim 3 wherein
    the anomaly is a defect in a nuclear power plant fluid containment component.

5. A method for detecting and charaterizing anomalies in radioactively-contaminated structures comprising:
    placing a gamma radiation detector in proximity to a surface of a structure to be examined, said detector being enclosed within a radiation-proof housing for uniformly shielding said detector, said housing including a beam slit formed therein having an external opening for admitting and for conducting radiation to said detector, said beam slit having a length and height such that an arctangent of said height divided by said length is approximately ten degrees or less whereby radiation entering said slit is collimated;
    scanning said surface while maintaining said detector in proximity to said surface, said scan being performed by positioning said beam slit opening close to and over said surface and displacing said housing relative to a preselected starting point;
    measuring and recording gamma radiation levels emitted by the structure at a plurality of points and angles about the structure, the measuring of gamma radiation including measuring at each point and angle the general background radiation and the radiation reading due to inside surface contamination and crack contamination and measuring and recording a location of said housing relative to said preselected started point for each radiation measurement, such that a plurality of data sets, comprising positional coordinates paired with radiation level values are generated; and
    analyzing said data sets by comparing a radiation level detected at each point with said level detected at each preceding point along each scan direction such that a graphical representation of the anomaly may be developed at each scan location.

* * * * *